United States Patent [19]

Molko et al.

[11] Patent Number: 5,204,456

[45] Date of Patent: Apr. 20, 1993

[54] DERIVATIVES OF NUCLEOSIDES AND THEIR USE FOR THE SYNTHESIS OF OLIGONUCLEOTIDES

[75] Inventors: Didier Molko, Tullins; Jean-Claude Schulhof, Saint Ismier; Robert Teoule, Grenoble, all of France

[73] Assignee: Commissariat a l'Energie Atomique, Paris, France

[21] Appl. No.: 585,507

[22] Filed: Sep. 20, 1990

Related U.S. Application Data

[63] Continuation of Ser. No. 31,781, Mar. 30, 1987, Pat. No. 4,980,460.

[30] Foreign Application Priority Data

Apr. 8, 1986 [FR] France ................................ 86 04990

[51] Int. Cl.$^5$ .................. C07H 19/067; C07H 19/073
[52] U.S. Cl. ................................ 536/25.33; 536/27.3; 536/27.81; 536/27.6; 536/27.5; 536/28.51; 536/26.71
[58] Field of Search ...................... 536/23, 24, 26, 27, 536/28, 29

[56] References Cited

U.S. PATENT DOCUMENTS

| | | | |
|---|---|---|---|
| 4,500,707 | 2/1985 | Caruthers et al. | 536/28 |
| 4,959,463 | 9/1990 | Froehler et al. | 537/27 |
| 4,980,460 | 12/1990 | Molko et al. | 536/23 |

FOREIGN PATENT DOCUMENTS 0196101 10/1986 European Pat. Off. .
0219342 4/1987 European Pat. Off. .

OTHER PUBLICATIONS

Hall et al., *J Chem. Soc.*, 1957, 3291-3296 (1957).
Kume et al., *J. Org. Chem.*, 49, 2139-2143 (1984).
Schulhof et al., *Nucleic Acids Research*, 15, 397-416 (1987).
Koster et al., *Tetrahedron*, 37, 363-369 (1981).
Schulhof et al. (II), *Nucleic Acids Research*, 16(1), 319-326 (1988).
Tran-Dinh et al., *Biochemistry*, 23, 1362-71 (1984).
Guy et al., *Helv. Chim. Acta*, 690, 1034-1040 (1986).
Koster et al. (II) *Nucleic Acid Research Symposium Series*, No. 7, IRL Press Limited, London, England, 1980, pp. 39-59.
Seliger et al., *Chem. Ber.*, 111(11), 3732-3739 (1978).
*Methods in Enzymology*, (1980), vol. 65, pp. 499-560, "Sequencing End-Labeled DNA with Base-Specific Chemical Cleavages", A. M. Maxam et al.
"The Chemical Synthesis of Oligo-and Poly-Nucleotides by the Phosphotriester Approach" by Collin B. Reese; Department of Chemistry, King's College, Strand, London WC2R 2LS, England, Apr., 1978.
"Nucleoside H-Phosphonates. III. Chemical Synthesis of Oligodeoxyribonucleotides by the Hydrogenphosphonate Approach" by Per J. Garegg et al; Pergamon Journals Ltd.; pp. 4051-4054.
"A Universal Glass Support for Oligonucleotide Synthesis" by J. S. deBear et al; Nucleosides & Nucleotides, 6(5), 821-830 (1987).
"Structure, Kinetics and Thermodynamics of DNA Hairpin Fragments in Solution", by C. A. G. Haasnoot et al; Journal of Biomolecular Structure and Dynamics, vol. 1, 1983; 115-129.
"Hairpin and Duplex Formation on the DNA Octamer d(m$^5$C-G m$^5$C-G-T-G-m$^5$C-G) in Solution. An NMR Study" by Orbons et al Nucleic Acids Research; pp. 4187-4196.
"H NMR and Circular Dichroism Studies of the B and Z Conformations of the Self-Complementary ." by Son Tran-Dinh et al Biochemistry 1984, 23, 1362-1371.

*Primary Examiner*—Johnnie R. Brown
*Assistant Examiner*—L. E. Crane
*Attorney, Agent, or Firm*—Oblon, Spivak, McClelland, Maier & Neustadt

[57] ABSTRACT

The invention relates to derivatives of nucleosides and their use for the synthesis of oligonucleotides. These derivatives are in accordance with the formula:

(Abstract continued on next page.)

ABSTRACT

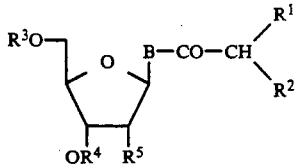 (I)

in which B represents a radical derived from guanine, cytosine or adenine, whose exocylic NH group is protected by the group

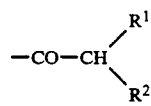

with $R^1$ representing a hydrogen atom or a alkyl radical and $R^2$ a hydrogen atom, and alkyl radical, an alkoxy radical and optionally substituted aryloxy radical, $R^3$ represents a hydrogen atom, the dimethoxytrityl radical or the radical

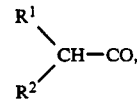

$R^4$ represents a hydrogen atom, the radical of formula:

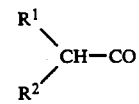

or a radical suitable for the synthesis of polynucelotides and $R^5$ represents a hydrogen atom or the protected or unprotected hydroxyl OH radical.

10 Claims, No Drawings

DERIVATIVES OF NUCLEOSIDES AND THEIR USE FOR THE SYNTHESIS OF OLIGONUCLEOTIDES

The instant application is a continuation application of U.S. Ser. No. 07/031,781, filed Mar. 30, 1987, now U.S. Pat. No. 4,980,460.

BACKGROUND OF THE INVENTION

The present invention relates to novel derivatives of nucleosides and their use for the synthesis of oligonucleotides.

It more specifically relates to derivatives of nucleosides formed from pyrimidine or purine bases having exocyclic $NH_2$ groups, i.e. nucleosides formed from adenine, guanine or cytosine, which can in particular be used for the synthesis of oligonucleotides.

The synthesis of oligonucleotides consists of linking together the nucleosides by a phosphate group to form an DNA (deoxyribonucleic acid) chain or RNA (ribonucleic acid) chain. In this bond, the internucleotide phosphate groups still link the hydroxyl function in the 3' position of a nucleoside with the hydroxyl function in the 5' position of another nucleoside. Thus, during the synthesis reaction only the 3' and 5' ends of the nucleosides are subject to an action and the nucleic base (purine or pyrimidine) used must not be involved during said bonding.

When these bases comprise exocyclic $NH_2$ groups, it is necessary to protect these groups during the synthesis of the oligonucleotides, because they are too reactive and may interfere with the synthesis reactions.

This protection of exocyclic $NH_2$ groups must satisfy the following : it must be selective and easy to carry out, it must not induce reactivity modifications to the other nucleoside sites and must be stable throughout the oligonucleotide synthesis stages and it must be eliminatable under gentle conditions without destroying the oligonucleotide which has been synthesized.

The exocyclic $NH_2$ groups of nucleosides have most frequently been protected in the form of amides, e.g. by means of benzoyl or anisoyl groups in the case of adenine and cytosine, as described by H. SCHALLER et al in J. Amer. Chem. Soc, 1963, vol 85, pp 3821–3827 and by means of the isobutyryl group in the case of guanine, as described by H. BÜCHI and H. KHORANA in J. Mol. Biol, 1972, vol 72, pp 251–288.

These protective groups can be eliminated at the end of synthesis by the action of 28% ammonia for 17 hours and at a temperature of 60° C., as has been recommended. However, the NMR of the proton shows that under these conditions all the isobutyryl groups of the guanine are not eliminated. It is therefore preferable to raise the reaction times to 72 hours, but still at a temperature of 60° C.

This procedure for eliminating protective groups constitutes a disadvantage, because the conditions used are not sufficiently gentle to permit use with modified nucleosides which are not very stable in the alkaline medium, as is e.g. the case with 5,6-dihydrothymidine.

Research has also been carried out on the possibility of using other acyl groups which are easier to eliminate, more particularly usable for the synthesis of oligonucleotides from unstable nucleosides by the methodology of synthesis on a support, which consists of fixing the first nucleoside of the chain to a support, generally of silica and then successively carrying out condensation cycles for fixing the other nucleosides in the desired order to the first nucleoside. The use of easier to eliminate acyl groups makes it possible to obtain a better deprotection yield. This point is very important, because the presence of incompletely deprotected bases constitutes a disadvantage for the use of the products obtained.

The present invention relates to novel derivatives of nucleosides having protective groups of the acyl type which can be easily eliminated.

SUMMARY OF THE INVENTION

The derivatives of nucleosides according to the invention comply with the formula:

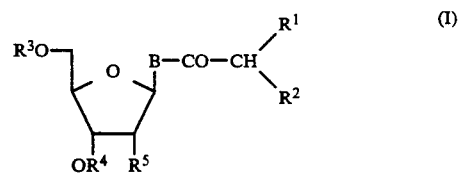

(I)

in which B represents a divalent radical chosen from among:

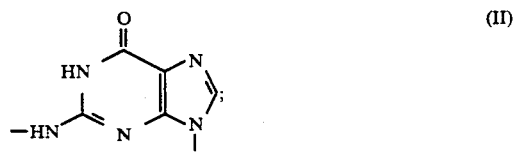

(II)

(III)

or

(IV)

connected to the CO group by its exocyclic NH group; $R^1$ representing a hydrogen atom or an alkyl radical, $R^2$ representing a hydrogen atom, an alkyl radical, an alkoxy radical, an aryloxy radical which is not substituted or substituted by or more groups chosen from among $NO_2$, CN, alkoxy, aryloxy,

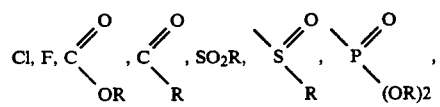

alkyl or aryl, which may be substituted or not, SR with R representing an alkyl or aryl radical, whilst excluding $R^1$=H and $R^2$=$CH_3$ when B is the radical (II) or (III) and $R^1=R^2=CH_3$ when B is the radical (II);

$R^3$ represents a hydrogen atom, an unstable radical in the acid medium or the radical of formula:

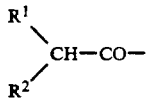

in which $R^1$ and $R^2$ have the meanings given hereinbefore, $R^4$ represents a hydrogen atom, a phosphorus radical or the radical:

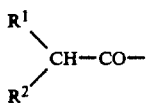

in which $R^1$ and $R^2$ have the meanings given hereinbefore and $R^5$ represents a hydrogen atom or the protected or unprotected OH radical.

For example, the unstable radicals in the acid medium which can be used for forming $R^3$ in the compound of formula (I) are in particular radicals usable in oligonucleotide synthesis, such as: the trityl radicals in accordance with the formula:

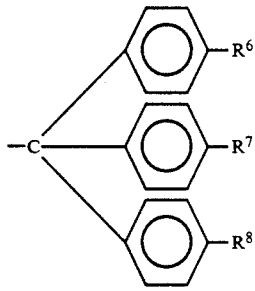
(V)

in which $R^6$, $R^7$ and $R^8$, which can be the same or different, represent a hydrogen atom, an alkyl radical or an alkoxy radical, e.g. the monomethoxytrityl radical or the trityl radical of formula (V) in which $R^6$ and $R^7$ represent the methoxy radical and $R^8$ represent a hydrogen atom; the pixyl radicals and 9-phenyl-xanthenyl radicals.

For example, the phosphorus radicals which can be used for forming $R^4$ in the compound of formula (I) are also radicals usable in oligonucleotide synthesis, such as the radical of formula:

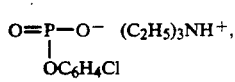
(VI)

the radical of formula:

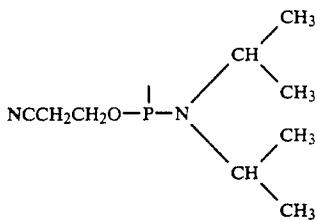
(VII)

or the phosphonate radical of formula:

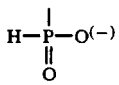

According to the invention, when $R^5$ represents the protected OH radical, the OH protective group is constituted by the groups conventionally used in the synthesis of ribonucleotides.

The derivatives of nucleosides according to the invention are thus the products of the union 1°) of a base formed by guanine, cytosine or adenine and 2°) ribose or deoxyribose, the nucleosides being modified at least on the exocyclic $NH_2$ group of their base by a group

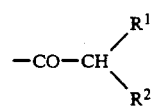

They can also be modified by said same group in the 3' and 5' positions of the deoxyribose or the 2', 3' and 5' positions of the ribose, or the 3' and 5' positions of the ribose or deoxyribose can be modified by other groups, which are unstable groups, $R^3$ for the 5' position and the phosphorus group $R^4$ on the 3' position of the ribose or deoxyribose.

The acyl groups of formula

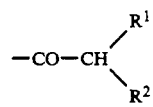

used in the invention are particularly interesting for the synthesis of nucleotides, because they can be easily eliminated at the end of the operation, e.g. by ammonia treatment for 2 to 8 hours as a function of the group used and at ambient temperature, which makes it possible to simultaneously free the polynucleotide of the support on which it has been synthesized, when use is made of the synthesis on support method.

In the protective group of formula

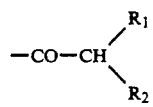

used in the invention, $R_1$ can be a hydrogen atom or an alkyl radical and $R_2$ a hydrogen atom, an alkyl radical, an alkoxy radical or an aryloxy radical optionally substituted by different groups.

The alkyl radicals which can be used for $R^1$ and $R^2$ can be straight or branched chain radicals, e.g. methyl, ethyl and similar radicals.

The alkoxy radicals which can be used for $R^2$ can also be straight or branched chain radicals. The aryloxy radicals which can be used can be in particular radicals derived from benzene, naphthalene and anthracene, e.g. the phenoxy radical and they may be substituted by one or more of the aforementioned substituents.

According to the invention, the protective group of the exocyclic $NH_2$ groups is chosen as a function of the base used, in order to obtain the desired resistance to alkaline treatment. Generally, when the base used is guanine, $R^1$ represents a hydrogen atom and $R^2$ is an alkoxy radical or an optionally substituted aryloxy radical. For example, the radical $R^2$ can be the phenoxy radical, methoxy radical or 2-chlorophenoxy radical.

When the base used is adenine, $R^1$ preferably represents a hydrogen atom and $R^2$ an optionally substituted aryloxy radical, e.g. the phenoxy radical.

When the base cytosine, the radicals $R^1$ and $R^2$ are preferably hydrogen atoms or alkyl radicals, e.g. methyl radicals.

The use of the aforementioned protective groups makes it possible to obtain a reduction in the deprotection times of the oligonucleotides obtained by bonding nucleosides according to the invention, because this time may only be 2 to 8 hours as a function of the group used, in place of the 17 to 72 hours previously required. It is also possible to operate under gentler reaction condition, because deprotection takes place at ambient temperature, whereas it was previously necessary to heat to 60° C. Moreover, the use of these more easily eliminatable protective groups makes it possible to incorporate during the synthesis of the oligonucleotides modified nucleic bases which are sensitive to more violent alkaline conditions, e.g. to synthesis DNA fragments carrying ligands sensitive to antibodies.

Although the invention applies to nucleosides derived from ribose and to nucleosides derived from deoxyribose. it is preferably used for nucleosides derived from deoxyribose, i.e. derivatives of formula (I) in which $R^5$ is a hydrogen atom.

The derivatives of nucleosides according to the invention can be prepared by conventional processes, identical to those used for fixing benzoyl and anisoyl groups to nucleosides based on adenine or cytosine. In these processes, one starts with the nucleoside of guanine, cytosine or adenine, which is reacted with the acid chloride of formula:

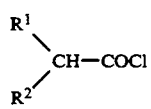

or the acid anhydride of formula:

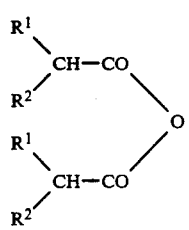

During this reaction, the acid chloride or anhydride also reacts with the hydroxyl groups in the 3' and 5' positions of the ribose or deoxyribose and thus the triprotected nucleoside derivative is obtained i.e. the derivative of formula (I) in which $R^3$ and $R^4$ both represent the radical:

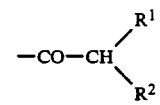

However, it is possible to eliminate these radicals in the 3' and 5' positions by selective hydrolysis, which makes it possible to obtain derivatives of nucleosides of formula (I) in which $R^3$ and $R^4$ represent hydrogen atoms.

It is possible to prepare derivatives of nucleosides of formula (I) in which $R^3$ represents a trityl radical of formula (V), e.g. the dimethoxytrityl group, and $R^4$ represents a hydrogen atom by reacting the derivatives of nucleosides obtained previously with the corresponding trityl chloride in an appropriate solvent.

The derivatives of nucleosides in accordance with formula (I), in which $R^3$ represents a trityl group and $R^4$ the radical of formula (VI) or the radical of formula (VII), or a radical of formula:

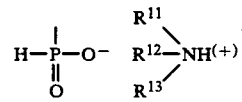

in which $R^{11}$, $R^{12}$ and $R^{13}$, which can be the same or different, are alkyl radicals, e.g. ethyl, can be prepared by conventional processes from derivatives of nucleosides of formula (I), in which $R^3$ represents a trityl radical and $R^4$ a hydrogen atom.

In the case where $R^4$ e.g. represents the radical of formula (VI), this nucleoside derivative is reacted with 4-chlorophenylphosphoryl bistriazolidate in an appropriate solvent. The 4-chlorophenylphosphoryl bistriazolidate can be prepared by adding 4-chlorophenyl dichlorophosphate to a suspension of triazole and triethylamine in dioxan.

When $R^4$ e.g. represents the radical of formula (VII), it is possible to react the nucleoside derivative with β-cyanoethyl-monochloro-N,N-diisopropyl-amino phosphoramidite in an appropriate solvent in the presence of diisopropylethylamine.

When $R^4$ e.g. represents the radical or formula:

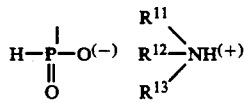

in which $R^{11}$, $R^{12}$ and $R^{13}$, which can be the same or different, are alkyl radicals, it is possible to react the nucleoside derivative with 2-chloro-(5,6-a)-benzo-[1, 3-dioxo-2-phosphor-4-inone] and then with a trialkyl ammonium salt, such as triethyl ammonium acetate.

The derivatives of nucleosides obtained by these three methods can be used for the synthesis of oligonucleotides either by phosphotriester synthesis in the case where $R^4$ is the radical of formula (VI), or by phosphoramidite synthesis in the case where $R^4$ is the radical of formula (VII), or by H-phosphonate synthesis in the case where $R^4$ is the radical of formula:

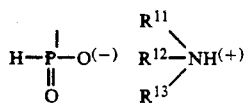

whilst also using for the bonding of the oligonucleotide chains other nucleosides, e.g. those corresponding to thymidine and 2'-deoxy uridine, or nucleosides having unstable bases in the alkaline medium or other unstable nucleosides in the alkaline medium.

The process according to the invention for the synthesis of oligonucleotides comprises:

1) at least one condensation cycle, in which on a nucleoside derivative or on an oligonucleotide is condensed a nucleoside derivative of formula:

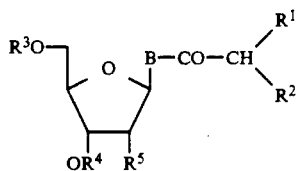

in which B represents a divalent radical chosen from among:

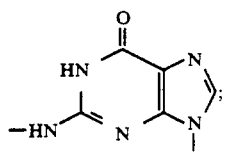

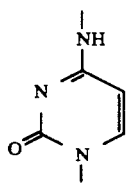

or

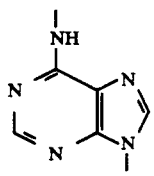

bonded to the CO group by its exocyclic NH group;

$R^1$ represents a hydrogen atom or an alkyl radical, $R^2$ represents a hydrogen atom, an alkyl radical, an alkoxy radical, an aryloxy radical which is unsubstituted or substituted by one or more groups chosen from among $NO_2$, CN, alkoxy, aryloxy, Cl, F,

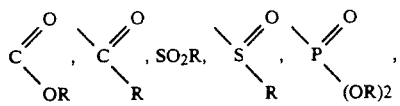

alkyl or aryl, which may or may not be substituted, SR with R representing an alkyl or aryl radical, excluding $R^1=H$ and $R^2=CH_3$ when B is the radical (II) or (III) and $R^1=R^2=CH_3$ when B is the radical (II);

$R^3$ represents a radical which is unstable in the acid medium, $R_4$ represents a phosphorus radical and $R^5$ represents a hydrogen atom; and 2) a stage for the elimination of the protective groups or groups of formula:

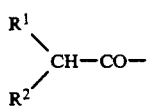

in which $R^1$ and $R^2$ are as defined hereinbefore, e.g. by contacting the oligonucleotide with ammonia at ambient temperature.

The oligonucleotide synthesis can be performed either by methods in solution, or by synthesis methods on a support. Preference is given to the use of synthesis methods on a support, because they are better adapted to the use of more unstable nucleosides, without there being any yield loss during bonding.

Thus, the nucleosides according to the invention have interesting uses as basic products used in the synthesis of DNA or RNA fragments. They may also be suitable for incorporation into synthesis oligonucleotides of fragile modified bases, which can in particular relate to the DNA gamma radiolysis products, as well photolysis products. The nucleosides according to the invention can also provide access to new molecules having an antiviral activity and to new DNA probes.

DESCRIPTION OF EXAMPLES OF THE INVENTION

The following examples concerning the preparation and use of nucleosides according to the invention are obviously given in a non-limitative manner.

EXAMPLE 1 : Preparation of ($N_2$-phenoxyacetyl)-2'deoxy guanosine (compound 1)

1080 mg (4 mmol) of 2'-deoxyguanosine are dried by successive additions and evaporations of anhydrous pyridine, they are then suspended in 20 ml of anhydrous pyridine and the suspension is then introduced into a flask. The flask is cooled by means of an ice bath and to it are slowly added six equivalents (4.25 g; 24 mmol) of phenoxyacetyl chloride at 0° C. The reaction is allowed to continue at ambient temperature for 90 minutes. A white pyridinium chloride precipitate appears in the reaction medium, whilst the latter assumes an orange to brown colouring. This gives the triprotected starting nucleoside derivative, i.e. the derivative of formula (I) in which $B_1$ represents the radical of formula (II) the guanine derivative, $R^1$ represents a hydrogen atom, $R^2$ represents the phenoxy radical $R^3$ and $R^4$ represent the phenoxyacetyl radical and $R^5$ is a hydrogen atom.

The acid chloride excess is then destroyed at 0° C. by 2 ml of bidistilled water, which solubilizes the reaction medium. It is then diluted with 100 ml of chloroform. The chloroform phase is washed four times with 50 ml of aqueous 5% sodium bicarbonate solution to eliminate the phenoxyacetic acid formed. The chloroform phase is then dried on sodium sulphate, the solvent evaporated and an orange residue is obtained. The latter is dissolved in 100 ml of pyridine cooled to 0° C., followed by the addition of 100 ml of 0.2N soda at 0° C. Thus, the selective hydrolysis of the 3' and 5' positions is carried out in 20 minutes. The medium is then neutralized by means of cation exchange resin Dowex 50W-X8 with a grain size of 100 to 200 mesh (0.074 to 0.149 mm) in the form of pyridinium. Following filtering and rinsing of the resin, the filtrate is evaporated to dryness.

This is followed by the isolation of the $N_2$-phenoxyacetyl-2'-deoxy guanosine formed by chromatography on silica column (diameter 3 cm, height 15 cm) which is eluted by a chloroform - methanol gradient. The evaporation of the fractions containing the sought product makes it possible to collect 250 mg of $N_2$-phenoxyacetyl-2'-deoxy guanosine, which corresponds to a 15% yield.

The identity and purity of the product obtained are controlled by nuclear magnetic resonance at 250 MHz, by thin layer chromatography and by mass spectrometry, the following results being obtained: $R_F=0.36$ with chloroform - methanol migration mixture (80/20 by volume), (M+H) molecular peak (m/e: 402 - 13%); phenoxyacetylated guanine (m/e: 286 - 51%).

EXAMPLE 2 : Preparation of [$N_2$-(2-chlorophenoxy)-acetyl]-2'-deoxy guanosine (Compound 2)

1080 mg (4 mmol) of 2'-deoxy guanosine are dried as in example 1, then suspended in 20 ml of anhydrous pyridine and introduced into a flask placed in an ice water bath. This is followed by the slow addition at 0° C. of six equivalents (5.1 g; 24 mmol) of (2-chlorophenoxy)-acetyl chloride. The reaction is allowed to continue at ambient temperature for 150 minutes. A green to chestnut colouring appears in the reaction medium and in this way the triprotected starting nucleoside derivative is formed, namely the derivative of formula (I) in which B represents the radical of formula (II), guanine derivative, $R^1$ represents a hydrogen atom, $R^2$ represents the 2-chlorophenoxy radical, $R^3$ and $R^4$ represent the 2-chlorophenoxy acetyl radical and $R^5$ is a hydrogen atom.

The acid chloride excess is destroyed at 0° C. by 2 ml of distilled water, which solubilize the reaction medium.

It is then diluted by 100 ml of chloroform and as said chloroform phase is washed four times with 50 ml of a 5% aqueous sodium bicarbonate solution in order to eliminate the chlorophenoxyacetic acid. The chloroform phase is dried on sodium sulphate, the solvent evaporated and in this way an orange residue is obtained. This residue is dissolved in 100 ml of pyridine, the solution obtained is placed in an ice water bath and 100 ml of 0.2N soda are added thereto, which gives a mixture titrating 0.1N and makes it possible to selectively hydrolyze the 3' and 5' positions of the nucleoside in 20 minutes. The medium is then neutralized by cation exchange resin Dowex 50W-X8 used in example 1 in pyridinium form. The resin is filtered and rinsed and then the filtrate evaporated to dryness. This gives [$N_2$-(2'chlorophenoxy)-acetyl]-2'-deoxyguanosine, which is only soluble in pyridine.

It is purified by chromatography on silica column using a chloroform - methanol gradient. Thus, 220 mg of compound 2 are isolated, which corresponds to a 13% yield. The compound is characterized by thin layer chromatography and mass spectrometry. The following results are obtained:

$R_4=0.4$ in a chloroform - methanol migration mixture (80/20 by volume), (M+H) molecular peak (m/e: 436 - 17%); 2-chlorophenoxyacetylated guanine (m/e: 320 - 44%).

The purity of the product is confirmed by analysis by nuclear magnetic resonance at 250 MHz.

EXAMPLE 3 : PREPARATION OF ($N_2$-METHOXYACETYL)-2'-DEOXYGUANOSINE (COMPOUND 3)

5.4 g (20 mmol) of deoxyguanosine are dried and then suspended in 100 ml of anhydrous pyridine. Cooling takes place to 0° C., followed by the slow addition of 4.5 equivalents (10 g; 90 mmol) of methoxyacetyl chloride. The reaction is allowed to continue at ambient temperature for 3 hours to form the triprotected derivative of the starting product, namely the derivative of formula (I) in which B represents the radical of formula (II) derived from guanine, $R^1$ represents a hydrogen atom, $R^2$ the methoxy radical, $R^3$ and $R^4$ the methoxyacetyl radical and $R^5$ a hydrogen atom.

The acid chloride excess is destroyed by methanol for 30 minutes, which produces methylmethoxyacetate with a low boiling point (129°-130° C.). The solvents are evaporated and the residue is taken up by chloroform. It is then washed by an aqueous 5% sodium bicarbonate phase. The chloroform phase is dried on sodium sulphate and then evaporated, so that an orange residue is obtained, which corresponds to the triprotected derivative.

The derivative is purified by silica column chromatography (diameter 4 cm, length 10 cm) using a chloroform - methanol gradient. Thus, 7 g of triprotected derivative are collected, which corresponds to a 73% yield.

The ester functions are then hydrolyzed by means of a mixture of triethylamine, pyridine and water (20:20:60 by volume). The solvents are then evaporated and the $N_2$-methoxyacetyl-2'-deoxyguanosine (compound 3) is purified by chromatography on a silanized silica column carrying out elution with a mixture of water and acetone (70:30 v/v). Thus, 3.4 g of product are obtained, which corresponds to a 51% yield. The product is checked by nuclear magnetic resonance at 250 MHz and mass spectrometry and the following results are obtained: (M - H): molecular peak (m/e: 338 - 10%); methoxyacetylated guanine: (m/e: 222 - 31%).

EXAMPLE 4 : Preparation of ($N_6$-phenoxyacetyl)-2'-deoxyadenosine (Compound 4)

1025 mg (4 mmol of deoxyadenosine are dried and then dissolved in 20 ml of anhydrous distilled pyridine and are introduced into a flask placed in an ice water bath. This is followed by the slow addition of 8 equivalents of phenoxyacetic anhydride (9.4 g; 32 mmol) dissolved in 20 ml of pyridine at 0° C. The reaction is allowed to continue at ambient temperature for 90 minutes and a yellowish colouring progressively appears. In this way the nucleoside derivative of formula (I) is formed, in which B represents the radical of formula (IV) derived from adenine, $R^1$ represents hydrogen, $R^2$ the phenoxy radical, $R^3$ and $R^4$ the phenoxyacetyl radical and $R^5$ a hydrogen atom.

The acid anhydride excess is then destroyed at 0° C. by adding 3 ml of distilled water and then the reaction medium is diluted by 100 ml of chloroform. The chloroform phase is washed 4 times by means of 50 ml of an aqueous 5% sodium bicarbonate solution and the solvent is evaporated, so that a yellow residue is obtained. The latter is dissolved in 100 ml of pyridine and, after placing the solution in an ice water bath, 100 ml of 0.2N soda are added at 0° C. in order to selectively hydrolyze the 3' and 5' positions of the adenosine in 15 minutes. The medium is then neutralized with the cation exchange resin Dowex 50W-X8 in the form of pyridinium used in example 1. The resin is filtered and rinsed and then the filtrate evaporated to dryness.

This gives ($N_6$-phenoxyacetyl)-2'-deoxyadenosine (compound 4), which is purified by silica column chromatography (diameter 4 cm, length 10 cm) using a chloroform - methanol gradient (100-0-96-4). The fractions containing the sought product are then evaporated and in this way 1010 mg of a whitish powder are obtained, which corresponds to a 65% yield.

The product is then characterized by thin layer chromatography, nuclear magnetic resonance of the proton at 250 MHz and mass spectrometry. The following results are obtained:

$R_F$: 0.66 with a chloroform - methanol migration mixture (80:20 by volume), nuclear magnetic resonance of the proton at 250 MHz: $^1$H-NMR (pyridine $d_5$): 2.7–3.3 (m, 2H, $H_2$, $H_{2''}$) ; 4.1–4.35 (m, 2H, $H_5H_{5''}$) ; 4.6 (m, $H_{4'}$) ; 5.25 (m, $H_{3'}$) ; 5.65 (s, 2H, $CH_2$) ; 7.0 (m, $H_{1'}$) ; 6.9–7.4 (m, 5H, $C_6H_5$) ; 8.75 and 9.05 (s, $H_2$ and $H_8$).

mass spectrometry: (M+H): molecular peak (m/e: 386 - 16%); acetylated phenoxy adenine (m/e: 270 - 66%).

EXAMPLE 5 : Preparation of ($N_4$-isobutyryl)-2'-deoxycytidine (Compound 5)

4 mmol of deoxycytidine are dried and then dissolved in 15 ml of anhydrous pyridine and the solution is introduced into a flask placed in an ice water bath. This is followed by the slow addition of 6 equivalents (2.5 ml; 24 mmol) of isobutyryl chloride. The reaction is allowed to continue at ambient temperature for 120 minutes and the medium takes on an orange colour. In this way the triprotected starting nucleoside derivative is formed, namely the derivative of formula (I), in which B represents the radical of formula (III) derived from cytosine, $R^1$ and $R^2$ the methyl radical, $R^3$ and $R^4$ the isobutyryl radical and $R^5$ a hydrogen atom.

The acid chloride excess is destroyed at 0° C. by 2 ml of bidistilled water and the reaction medium diluted by 100 ml of chloroform. The chloroform phase is washed 4 times with 50 ml of 5% sodium bicarbonate solution in order to eliminate the isobutyric acid formed, drying takes place on sodium sulphate, followed by evaporation to dryness.

This gives an orange residue, which is dissolved in 5 ml of pyridine cooled to 0° C. This is followed by the addition of 100 ml of 0.2N soda at 0° C. and the selective hydrolysis reaction of the ester functions in the 3' and 5' positions of the deoxyribose is allowed to continue for 30 minutes. This is followed by the neutralization of the medium with ion exchange resin Dowex 50W-X8 in the form of pyridinium used in example 1. This is followed by the filtration and rinsing of the resin and the evaporation to dryness of the filtrate.

Purification takes place by silica column chromatography (diameter 4 cm, length 10 cm) using a chloroform - methanol gradient (100-0 to 95-5). The solvents are evaporated and in this way 630 mg of a white powder are obtained constituted by isobutyryl-deoxycytidine, which corresponds to a 50% yield.

The product is characterized by thin layer chromatography, mass spectrometry and nuclear magnetic resonance of the proton at 250 MHz. The following results are obtained:

$R_F$: 0.55 with chloroform - methanol migration mixture (80:20), mass spectrometry (M+H): molecular peak (m/e=298-11%), isobutyrylated cytosine (m/e=182-100%), nuclear magnetic resonance of the proton at 250 MHz: $^1$H-NMR (methanol $d_4$): 1.2 (d, 6H, 2($CH_B$) of ib.), 2.15–2.6 (m, 2H, $H_{2'}$, $H_{2''}$), 2.7 (m, $H^i$) ; 3.7–3.9 (m, 2H, $h_{5'}$, $H_{5''}$) ; 4.0 (m, $H_4$) ; 4.4 (m, $H_{3'}$) ; 6.25 (t, $H_{1'}$) ; 7.5 and 8.5 (d, $H_5$ and $H_6$).

EXAMPLE 6 : Preparation of ($N_4$-isobutyryl)-5'-(4,4'dimethoxytrityl)-2'deoxycytidine (Compound 6)

2.5 mmol of compound 5 are dried by successive additions and evaporations of anhydrous pyridine. There is taking up with 25 ml of pyridine, cooling to 0° C. and the addition of 2.75 mmol (1.1 equivalent) of 4,4'-dimethoxy trityl chloride in 25 ml of pyridine at 0° C. The reaction is allowed to continue for 17 hours at 5° C. and then 2 ml of methanol are added to the reaction medium. After 30 minutes, the solvent is expelled with the rotary evaporator and the oily residue taken up by 100 ml of ethyl acetate, followed by washing 3 times with 50 ml of aqueous 5% $NaHCO_3$ solution and once with 50 ml of bidistilled water. The organic phase is then dried on sodium sulphate and concentrated. By fractionating on a silica gel column, the thus obtained compound 6 is isolated and corresponds to formula (I), in which B is radical of formula (III) derived from cytosine, $R^1$ and $R^2$ are methyl radicals, $R^3$ the 4,4-'dimethoxy trityl radical, $R^4$ a hydrogen atom and $R^5$ a hydrogen atom.

The physicochemical characteristics of this compound and the reaction yield are given in table 1.

EXAMPLE 7 : Preparation of ($N_6$-phenoxyacetyl)-5'-(4,4'-dimethoxy trityl)-2'-deoxy adenosine (Compound 7)

The same operating procedure as in example 6 is adopted, but using 2.5 mmol of compound 4 in place of compound 5 and in this way compound 7 is produced: ($N_6$-phenoxyacetyl) 5'-(4,4'-dimethoxy trityl)-2'-deoxy adenosine, i.e. the compound in accordance with formula (I), in which B is the radical derived from adenine of formula (IV), $R^1$ is a hydrogen atom, $R^2$ the phenoxy radical, $R^3$ the 4,4'-dimethoxy trityl radical, $R^4$ a hydrogen atom and $R^5$ a hydrogen atom.

The reaction yield and the physicochemical characteristics of the compound are given in table (I).

EXAMPLE 8 : Preparation of ($N_2$-methoxyacetyl)-5'-(4,4'-dimethoxy trityl)-2'-deoxy guanosine) Compound 8)

The same operating procedure as in example 6 is adopted, but using 2.5 mmol of compound 3 in place of compound 5.

This gives compound 8 in accordance with formula (I), in which B is the radical of formula (II) derived from guanine, $R^1$ is hydrogen atom, $R^2$ the methoxy radical, $R^3$ the 4,4-dimethoxy trityl radical, $R^4$ a hydrogen atom and $R^5$ a hydrogen atom.

The reaction yield and physicochemical characteristics of this compound are given in table 1. In this table, the bracketed letter indicate the multiplicity of the peak with s=singlet, d=doublet, t=triplet, q=quadruplet and m=multiplet.

EXAMPLE 9 : Preparation of Compound 9

This example illustrates the preparation of a phosphoryl derivative of compound 8 used for phosphotriester synthesis of polynucleotides.

3 mmol of compound 8 are dried by adding and evaporating anhydrous pyridine (3 times 5 ml). The residue is taken up in 15 ml of pyridine and 4.5 mmol of 4-chlorophenylphosphoryl bistriazolidate in 30 ml of anhydrous dioxan (the 4-chlorophenylphosphoryl bistriazolidate was obtained by adding 4.5 mmol of 4-chlorophenyl dichlorophosphate to a suspension of 9 mmol of triazole and 9.35 mmol of triethylamine in 30 ml of dioxan). The reaction is allowed to continue for 20 minutes and is then stopped by adding 6 ml of a $H_2O$-triethylamine mixture (1:1 by volume) and then the volume of the reaction medium is reduced to 5 ml by evaporation. This is followed by taking up in 100 ml of chloroform and washing 3 times with 50 ml of an aqueous $NaHCO_3$ solution and then with 100 ml of water. The chloroform phase is dried on sodium sulphate and then evaporated to dryness. The sought compound is isolated by silica gel chromatography. The product obtained is then controlled by mass spectrometry and nuclear magnetic resonance. The reaction yield and the results obtained are given in table 2.

The compound 9 obtained in this way is the nucleoside derivative of formula (I), in which B represents the radical derived from guanine of formula (II), $R^1$ a hydrogen atom, $R^2$ the methoxy radical, $R^3$ the 4,4'-dimethoxy trityl radical, $R^4$ the radical of formula (VI) and $R^5$ a hydrogen atom.

EXAMPLE 10 : Preparation of Compound 10

This example adopts the same operating procedure as in example 9 for preparing the phosphoryl derivative for phosphotriester synthesis of compound 7 using 2.5 mmol of compound 7 in place of 2.5 mmol of compound 8. This gives compound 10, which is in accordance with formula (I), in B represents the radical of formula (IV) derived from adenine, $R^1$ a hydrogen atom, $R^2$ the phenoxy radical, $R^3$, the 4,4'-dimethoxy trityl radical, $R^4$ the radical of formula (VI) and $R^5$ a hydrogen atom.

As hereinbefore, the characteristics of the compound obtained are controlled by mass spectrometry and nuclear magnetic resonance, the results obtained and the reaction yield being given in table 2.

EXAMPLE 11 : Preparation of Compound 11

In this example, the operating procedure of example 9 is adopted for preparing the phosphoryl derivative of compound 6 used for phosphotriester synthesis using 3 mmol of compound 6 in place of 3 mmol of compound 8.

This gives compound 11 in accordance with formula (I), in which B represents the radical of formula (III) derived from cytosine, $R^1$ and $R^2$ the methyl radical, $R^3$ the 4,4'-dimethoxy trityl radical, $R^4$ the radical of formula (VI) and $R^5$ a hydrogen atom.

As in examples 9 and 10, the product obtained is checked by mass spectrometry and nuclear magnetic resonance. The reaction yield and the results obtained are given in table 2.

EXAMPLE 12: Preparation of Compound 12

In this example is prepared the phosphoryl derivative of compound 8 used for oligonucleotide phosphoramidite synthesis.

3 mmol of compound 8 are dried by co-evaporation of pyridine, toluene and tetrahydrofuran (THF). The residue is taken up in 15 ml of THF in the presence of 12 mmol of N, N, N-diisopropylethylamine and this is followed by the dropwise addition in 2 minutes of 6 mmol of β-cyanoethyl-monochloro-N,N-diisopropylaminophosphoramidite. After 5 minutes reaction, there is a formation of a hydrochloride precipitate of the amine. The reaction is allowed to continue for 35 minutes and the precipitate is filtered at the end of the reaction. The filtrate is then evaporated to dryness and taken up in 150 ml of ethyl acetate. Washing takes place by a iced aqueous solution containing 10% of $Na_2CO_3$. The organic phase is then washed on sodium sulphate and evaporated to dryness.

The compound obtained is purified by low pressure chromatography on a MERCK "LOBAR" column of size B using for the elution a mixture of $CH_2Cl_2$-hexane-triethylamine (70:20:10 by volume). The compound obtained is taken up by a minimum of dichloromethane or ethyl acetate and is precipitated in hexane at $-80°$ C. The product is analysed by nuclear magnetic resonance. The results obtained and the reaction yield are given in table 3.

This gives compound 12, which complies with formula (I), in which B represents the radical of formula (II) derived from guanine, $R^1$ a hydrogen atom, $R^2$ the methoxy radical, $R^3$ the 4,4'-dimethoxy trityl radical, $R^4$ the radical of formula (VII) and $R^5$ a hydrogen atom.

EXAMPLE 13 : Preparation of Compound 13

As in example 12, the phosphoryl derivative of compound 7 is prepared and this is to be used for phosphoramidite synthesis using 3 mmol of compound 7 in place of 3 mmol of compound 8. Analysis also takes place of the product obtained by nuclear magnetic resonance. The yield of the reaction and the results are given in table 3.

This gives compound 13 complying with formula (I), in which B is the radical of formula (IV) derived from adenine, $R^1$ a hydrogen atom, $R^2$ the phenoxy radical, $R^3$ the 4,4'-dimethoxy trityl radical, $R^4$ the radical of formula (VII) and $R^5$ a hydrogen atom.

EXAMPLE 14 : Preparation of Compound 14

As in example 12, the phosphoryl derivative of compound 6 is prepared, which is intended for phosphoramidite synthesis using 3 mmol of compound 6 in place of 3 mmol of compound 8. The product obtained is also analyzed by nuclear magnetic resonance. The reaction yield and results obtained are given in table 3.

This gives compound 14 complying with formula (I), in which B represents the radical of formula (III) derived from cytosine, $R^1$ and $R^2$ the methyl radical, $R^3$ the 4,4'-dimethoxy trityl radical, $R^4$ the radical of formula (VII) and $R^5$ a hydrogen atom.

EXAMPLE 15 : Preparation of (N6-phenoxyacetyl)-5'-(4, 4'-dimethoxy trityl)-2'-deoxyguanosine (compound 15)

The same operating procedure as in example 6 is adopted using 4 mmol of compound 1 in place of compound 5 and in this way compound 15 is produced, i.e. the compound complying with formula (I), in which B is the radical derived from guanine of formula (II), $R^1$ is a hydrogen atom, $R^2$ the phenoxy radical, $R^3$ the 4,4'-dimethoxy trityl radical, $R^4$ a hydrogen atom and $R^5$ a hydrogen atom.

The reaction yield is 70%. The Rf of this compound in the chloroform: methanol mixture (90:10) is 0.40. The chemical displacements of the main protons of this molecule in deuterated methanol have the following values: H8: 8.07 ppm, H1': 6.45 ppm (t), H3', 4.75 ppm (m), H CH3 of dimethoxy trityl: 3.86 ppm (s), H CH2 of phenoxyacetyl: 5.05 ppm (s).

EXAMPLE 16 : Preparation of Compound 16

As in example 12, the phosphoryl derivative of compound 15 is prepared, intended for phosphoramidite synthesis using 3 mmol of compound 15 in place of 3 mmol of compound 8. The finished product yield is 50%. The product is characterized by a NMR doublet of the 31P localized at 146 and 146.2 ppm in the deuterated pyridine. The main NMR peaks of the proton in deuterated acetonitrile are localized at: 8.12 ppm (s, H8), 6.45 ppm (t, H1'), 5.05 ppm (s, CH2 phenoxyacetyl) and 4.88 ppm (m, H3'). By mass spectrometry using a FAB ion source, it is possible to observe the molecular peak of this product for a value m/e of 903.

This gives compound 16 complying with formula (I), in which B is the radical derived from the guanine of formula (II), $R^1$ is a hydrogen atom, $R^2$ the phenoxy radical, $R^3$ the 4,4'-dimethoxy trityl radical, $R^4$ the phosphorus radical of formula (VII) and $R^5$ a hydrogen atom.

The following examples 17 to 19 illustrate the preparation of completely protected mononucleotides used for the synthesis of oligonucleotides according to the H-phosphonate method.

EXAMPLE 17 : Preparation of Compound 17

Compound 17 for the synthesis of oligonucleotides is prepared according to the H-phosphonate method. 5 mmol of compound 7 are dried by co-evaporation of 5 ml of anhydrous dioxan and they are taken up in 15 ml of said solvent and 5 ml of anhydrous pyridine. This is followed by the addition of 5 ml of a solution of 1.25 M 2-chloro-(5,6-a)-benzo-[1,3-dioxo-2-phosphor-4-inone] or salicylchlorophosphite of formula:

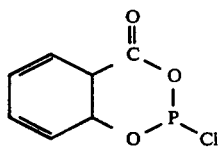

and the reaction is allowed to continue for 10 minutes at ambient temperature.

This is followed by the addition of 0.5 ml of water and hydrolysis is allowed to evolve for 10 minutes. This mixture is then poured into 250 ml of molar aqueous triethylammonium acetate solution and the desired product is extracted with twice 250 ml of chloroform. The organic phase is dried with anhydrous sodium sulphate and concentrated with the rotary evaporator. The thus obtained residue is purified by high performance liquid chromatography on a silica gel column (200x40 mm). The product is eluted with solutions having an increasing methanol concentration in a 2% triethylamine mixture in chloroform (0% methanol: 250 ml ; 1% methanol: 250 ml ; 2% methanol: 250 ml; 3% methanol: 250 ml ; 5% methanol : 250 ml ; 7% methanol : 500 ml). The fractions containing the sought product are collected and the solvent evaporated to obtain a product in the form of a white foam. The yield of product 17 is 55%. The product is analysed by nuclear magnetic resonance and the results obtained are given in table (IV).

This gives compound 17 complying with formula (I), in which B represents the radical of formula (IV) derived from adenine, $R^1$ a hydrogen atom, $R^2$ the phenoxy radical, $R^3$ the 4,4'-dimethoxy trityl radical, $R^4$ the phosphorus radical of formula

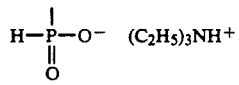

and $R^5$ a hydrogen atom.

EXAMPLE 18 : Preparation of Compound 18

As in example 17, the phosphoryl derivative of compound 15 is prepared and which is intended for oligonucleotide synthesis according to the H-phosphonate method using 5 mmol of compound 15 in place of 5 mmol of compound 7. The reaction yield is 48% and the product obtained is analyzed by nuclear magnetic resonance. The results obtained are given in table (IV).

This gives compound 18 complying with formula (I), in which B represents the radical of formula (II) derived from guanine, $R^1$ represents a hydrogen atom, $R^2$ the phenoxy radical, $R^3$ the 4,4'-dimethoxy trityl radical, $R^4$ the phosphorus radical of formula

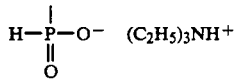

and $R^5$ a hydrogen atom.

EXAMPLE 19 : Preparation of Compound 19

As in example 17, the phosphoryl derivative of compound 5 is prepared and is used for oligonucleotide synthesis according to the H-phosphonate method using 5 mmol of compound 5 in place of 5 mmol of compound 7. The reaction yield is 62% and the product obtained is analyzed by nuclear magnetic resonance. The results obtained are given in table (IV).

This gives compound 19 complying with formula (I), in which B represents the radical of formula (III) derived from cytosine, $R^1$ and $R^2$ the methyl radical, $R^3$ the 4,4'-dimethoxy trityl radical, $R^4$ the phosphorus radical of formula

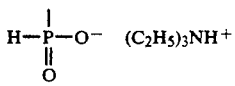

and $R^5$ a hydrogen atom.

EXAMPLE 20

This example illustrates compounds 9, 10 and 11 for the synthesis of an oligonucleotide, whose sequence is as follows:

d(AATTCAGATUTGATCAT) AGRE-AGRE

In this sequence, A represents the nucleotide formed with adenine, C the nucleotide formed with cytosine and G the nucleotide formed with guanine, T the nucleotide formed with thymine and U the nucleotide formed with uracil.

For carrying out this synthesis, use is made of compounds 9, 10 and 11 as synthons corresponding respectively to guanine, adenine and cytosine and the synthons corresponding to thymine and uracil. The latter are obtained from the corresponding nucleosides by protecting the hydroxyl functions in the 5' and 3' positions respectively by the 4,4'-dimethoxytrityl radical and the radical of formula (VI) using the same operating procedure as in example 6 to 11.

Synthesis is performed by means of a Biosearch SAM ONE automaton using 50 mg, i.e. approximately 1.5 to 3 mol of the support comprising the end 5' of the chain (Pierce "Controlled Pore Glass"), 25 mg per condensation cycle of nucleoside derivatives obtained in examples 9 to 11 and thymidine and 2'-deoxyuridine synthons, which represent approximately 8 to 15 equivalents and 25 mg per condensation cycle, i.e. 2 equivalents with respect to the nucleoside of an activating agent constituted by mesitylene sulphonyl chloride.

The following stages constitute each condensation cycle: detritylation: 2% trichloroacetic acid in $CH_2Cl_2$ for 2 minutes, washing: $CH_3CN$ for 1 minute, drying: anhydrous $CH_3CN$ for 6 minutes, condensation: monomeric nucleoside derivative and mesitylene sulphonyl chloride in a $CH_3CN$/1-methyl imidazole mixture (85:15 by volume) for 15 minutes and washing: $CH_3CN$ for 6 minutes.

Thus, at the end of these condensation cycles a silica gel is obtained containing the covalently bonded oligonucleotide. It is all transferred into a Pyrex flask, followed by the addition of 28% ammonia and is left for 8 hours at ambient temperature. The oligonucleotide is thus freed from the support by also eliminating the protective groups forming the object of the invention.

The supernatant is then removed and the silica is rinsed 3 times with 1 ml of bidistilled water. The solvent is evaporated and the residue is taken up in 0.5 ml of water followed by fractionation on a Sephadex G 25 column (diameter 1 cm, height 7 cm). The fractions representing an absorption in the ultraviolet at 254 nm are collected and lyophilized.

By phosphorus 32 marking using T4-polynucleotide kinase and by electrophoresis on polyacrylamide gel, the satisfactory length of the synthetic DNA fragment obtained is checked. The cutting of the corresponding strip and the elution of the compound make it possible to purify the product with a view to biological use.

In the same way, preparation takes place of the oligonucleotides having the following sequences:
d(AATTCAGAUCTGATCAT),
d(AATTCAGUTCTGATCAT),
d(AATTCAUATCTGATCAT), and
d(CGATGATCAGATCTG).

Once again good results are obtained, together with the elimination of the protective groups under gently conditions in ammonia at ordinary temperature.

EXAMPLE 21

In this example use is made of compounds 12, 13 and 14 for synthesizing homopolymers of 15 nucleotides long using phosphoramidite synthesis.

Syntheses are performed with the aid of the same biosearch SAM ONE automaton as in example 20 and the following reagent quantities are used: 50 g, i.e. 1.5 to 3 mol of the support used in example 15 comprising end 3' of the polynucleotide chain, 20 mg of compounds 12, 13 or 14 per condensation cycle (20 to 25 equivalents) and 15 mg per condensation cycle (2 equivalents with respect to the nucleotide) of an activating agent constituted by 5-paranitrophenyl tetrazole.

Each condensation cycle comprises the following stages: detritylation: 2% trichloroacetic acid in $CH_2Cl_2$ for 90 seconds, washing: $CH_3CN$ for 1 minute, drying: anhydrous $CH_3CN$: anhydrous dimethylformamide (90:10) for 3 minutes, condensation: nucleoside derivative + activating agent in $CH_3$/CN: dimethylformamide mixture (90:10) for 3 minutes, oxidation: 0.45% iodine in tetrahydrofuran: water: lutidine (89.5:10:0.5) for 1 minute, masking the hydroxyl functions which have not reacted for stopping the elongation of the incomplete chains. Mixture of acetic anhydride and 1-methyl imidazole in anhydrous $CH_3CN$ for 2 minutes, washing: $CH_3CN$ for 3 minutes.

After 14 condensation cycles carried out with the same compound (compounds 12, 13 or 14), the support incorporating the synthesized product is transferred into a Pyrex flask and 2 ml of 28% ammonia are added. The flasks are kept at ambient temperature for 8 hours, which makes it possible to eliminate the protective groups forming the object of the invention.

The supernatant is then taken and the silica is rinsed 3 times with 1 ml of bidistilled water, the solvent then being expelled with the rotary evaporator. The crude residue is taken up in 0.5 ml of water and is purified by chromatography on Sephadex G 25 gel. The fractions absorbing at 254 nm are collected and their content is analyzed by electrophoresis on polyacrylamide gel after phosphorus 32 marking using T4-polynucleotide kinase.

Thus, it is possible to check that the 3 synthesized homopolymers have the desired length and that they respectively correspond to $d(A_{15})$, $d(C_{15})$ and $d(G_{15})$.

EXAMPLE 22 : Preparation of an Oligonucleotide by the H-Phosphonate Method

This example illustrates the use of compounds 17, 18 and 19 for the synthesis of an oligonucleotide having the following sequence:

5' d(ATGATCTACT) 3'

In this sequence, A, G, C and T represent the same nucleotides as in the sequence of example 20.

In order to carry out bonding, compounds 17, 18 and 19 are used as synthons respectively corresponding to adenine, guanine and cytosine and a synthon corresponding to thymine. The latter is obtained from thymidine by protecting the 5' function with a 4,4'-dimethoxy trityl group and the 3' function by the phosphorus group of formula $$H-P-O\ (C_2H_5)_3NH^+$$

by using the same operating procedure as that described hereinbefore for the H-phosphonate derivative of adenine.

Bonding takes place by means of a biosearch SAM ONE automaton using: a column which has been preconditioned by the designer comprising a support grafted with one micromole of thymidine protected in the 5' position by a 4,4'-dimethoxy trityl group, 8 mg per condensation cycle of nucleoside derivatives 17, 18 and 19 and the corresponding thymidine derivative, which represents approximately 10 molar equivalents and 6 microlitres per condensation cycle, i.e. 50 molar equivalents of trimethyl acetyl chloride, used as the activating agents.

The stages of each condensation cycle are as follows: 2% trichloroacetic acid in dichloromethane, 3 ml in 1 minute, washing with acetonitrile: 3 ml, drying with a pyridine: acetonitrile mixture 1: 1, i.e. 3 ml, condensation: nucleoside derivative and activating agent in 2 ml of pyridine - acetonitrile mixture in 1 minute, washing with 3 ml of pyridine - acetonitrile mixture, washing with 3 ml of acetonitrile.

At the end of the condensation cycles, the internucleotide phosphorus oxidation takes place by passing a 2% iodine solution into a pyridine: water mixture 98:2 (3 ml). This is followed by washing with the mixture of pyridine and acetonitrile (5 ml), by acetonitrile (3 ml) and then detritylation, in the manner described hereinbefore.

This gives a silica gel comprising the covalently bonded polynucleotide. This is all transferred into a Pyrex flask, 2 ml of 28% ammonia are added and is left for 2 hours at ordinary temperature. Thus, the oligonucleotide is freed from the support, whilst also eliminating the protective groups forming the object of the invention. The supernatant is then taken, the silica rinsed 3 times with 1 ml of bidistilled water, the solvent is evaporated and the residue taken with 0.5 ml of water. This is followed by fractionation on Sephadex G25 column (diameter 1 cm, height 7 cm), followed by the combination of the fractions having an absorption in the ultraviolet at 254 nm and the lyophilization thereof.

The correct length of the synthesized product is checked by radioactive phosphorus 32 marking using the T4-polynucleotide kinase, followed by electrophoresis in polyacrylamide gel.

TABLE I

| | | NMR Spectrometry $^1$H at 250 MHz in ppm in CD$_3$OD + TMS | | | | |
|---|---|---|---|---|---|---|
| Compound | yield | H$_1'$ | H$_3'$ | CH$_3$ (trityl) | Base | Base protection |
| 6 | 74% | 6.15(t) | 4.5(q) | 3.7(s) | H$_5$ = 7.4(d).H$_s$ = 8.3(d) | CH$_3$ (isobutyryl) = 1.15(d.d) |
| 7 | 51% | 6.51(t) | 4.68(m) | 3.72(d) | H$_2$, H$_s$ = 8.46–8.57(s) | CH$_2$ (phexoxyacetyl) = 4.97(s) |
| 8 | 76% | 6.33(t) | 4.57(m) | 3.72(s) | H$_s$ = 8.04(s) | CH$_2$ (methoxyacetyl) = 4.13(s) |
| | | | | | | CH$_3$ (methoxyacetyl) = 3.46(s) |

TABLE II

| | | | | Sugar | | NMR$_1$H | |
|---|---|---|---|---|---|---|---|
| Compound | Yield | Mass spect | NMR$^{31}$P$^{b)}$ | H$_1'$ | H$_3'$ | Base | Amide protection |
| 9 | 30% | 830(2.3%) | −5.0 | 6.36(t) | 5.19(m) | H$_8$(s) = 8.03 | CH$_2$ = 4.13(s) |
| | | | | | | | CH$_3$ = 3.46(s) |
| 10 | 72% | 876(6.7%) | −5.5 | 6.56(t) | 5.28(m) | H$_2$, H$_8$(s) = 8.53 and 8.42 | CH$_2$ = 5.01(s) |
| 11 | 67% | 788(2.7%) | −5.3 | 6.22(t) | 5.20(m) | H$_5$(d) = 7.56 | CH$_3$ (isobutyryl)(d,d) = 1.16 |
| | | | | | | H(d) = 8.19 | |

Table II:
$^{a)}$negative ion FAB source. Measuring the mass of the phosphodiester peak.
$^{b)}$chemical displacements indicated in ppm relative to H$_3$PO$_4$, 85% taken as external reference.

TABLE III

| | | | | Sugar | | NMR$_1$H at 250 MHz$^{a)}$ CD$_3$CN |
|---|---|---|---|---|---|---|
| Compound | Yield | NMR$^{31}$P$^{b)}$ | H$_1'$ | H$_3'$ | Base | Amide |
| 12 | 51% | 155.3 | 6.26 | 4.69 | H$_8$ = 7.87 | CH$_2$ = 4.12 |
| | | 155.2 | | | | CH$_3$ = 3.45 |
| 13 | 53% | 155.3 | 6.44 | 4.93 | H$_2$, H$_8$ = 8.28; 8.56 | CH$_2$ = 4.99 |
| 14 | 85% | 155.3 | 6.14 | 4.60 | 8.14; 8.21 | CH$_3$ (isobutyryl) = 1.07 |

Table III:
$^{a)}$the compounds are in the form of a mixture of two diasterioisomers and the NMR$^1$H spectra are difficult to interpret.

TABLE IV

| | | | | NMR of proton | |
|---|---|---|---|---|---|
| Compound | NMR 31P (ppm) | H$_1'$ | Sugar H$_3'$ | Base | protection |
| 17 | 3.66 | 6.95 m | 5.66 m | H8 and H2 8.81 s 8.75 s | 5.69 s |
| 18 | 2.26 | 6.63 t | 5.30 m | H8 8.40 s | 5.71 s |
| 19 | 3.62 | 6.77 t | 5.60 m | H6 and H5 8.53 d 7.61 d | 1.25 dd |

Spectra recorded in deuterated pyridine.

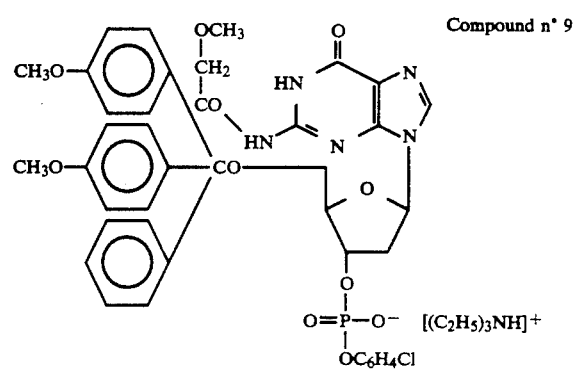

Compound n° 9

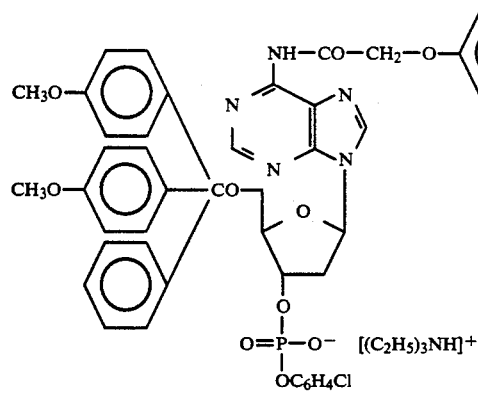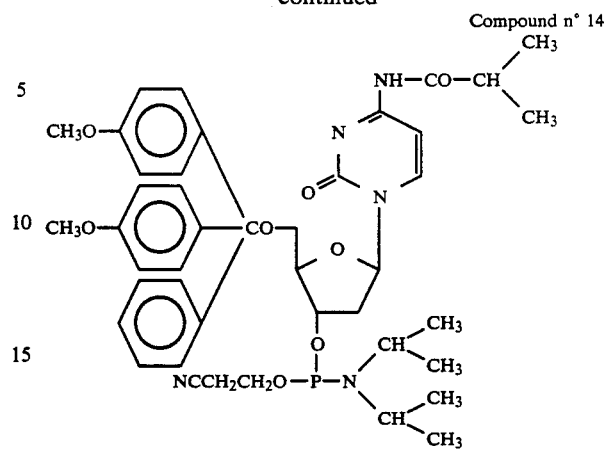

What is claimed is:

1. A nucleoside having the formula:

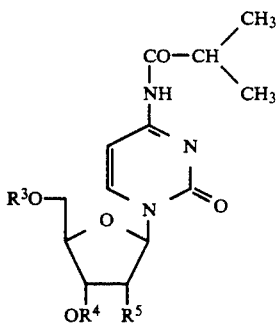

wherein

R³ is selected from the group consisting of hydrogen, 9-phenylxanthenyl, trityl of the formula

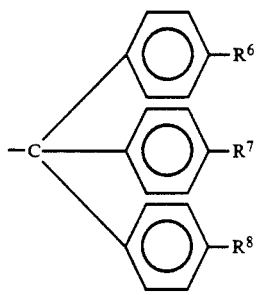

wherein R⁶, R⁷, and R⁸ which may the same or different, are hydrogen, methyl, ethyl or methoxy, and the group of formula:

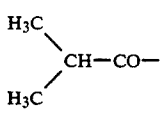

R⁴ is hydrogen, a phosphorylated group selected from the group consisting of phosphate, H-phosphonate and phosphoramidite, and the group

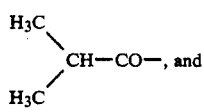

R⁵ is hydrogen, OH or a protected OH group.

2. The nucleoside according to claim 1, wherein R⁴ is selected from the group consisting of groups of the formula:

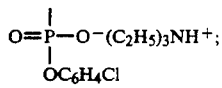

-continued

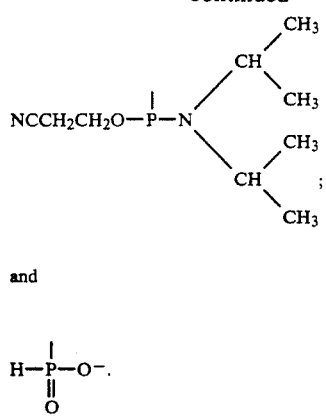

and

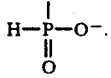

3. The nucleoside according to claim 1, wherein R³ and R⁴ are hydrogen.

4. The nucleoside according to claim 1, wherein R³ is the group:

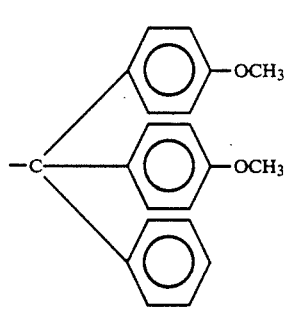

and R⁴ is hydrogen.

5. The nucleoside according to any one of the claims 1 to 4, wherein R⁵ is hydrogen.

6. The nucleoside according to claim 1, wherein R³ is the group:

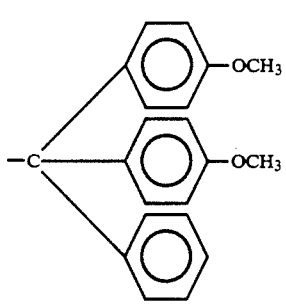

and R⁴ is the group:

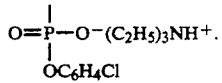

7. The nucleoside according to claim 1, wherein R³ is the group:

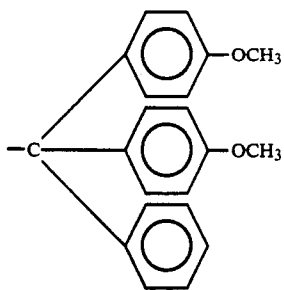

and R⁴ is the group:

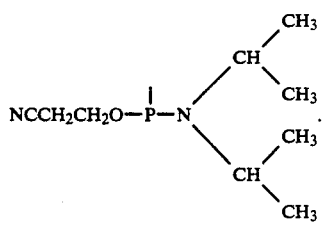

8. The nucleoside according to claim 1, wherein $R^3$ is the group:

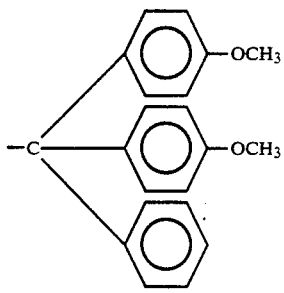

and R⁴ is:

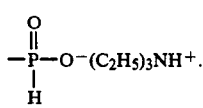

9. The nucleoside according to any one of the claims 6 to 8, wherein $R^5$ is hydrogen.

10. In a process for the synthesis of oligonucleotides, by condensing a protected nucleoside on a nucleoside or an oligonucleotide, wherein the improvement comprises the steps of:

1) condensing a nucleoside of the formula:

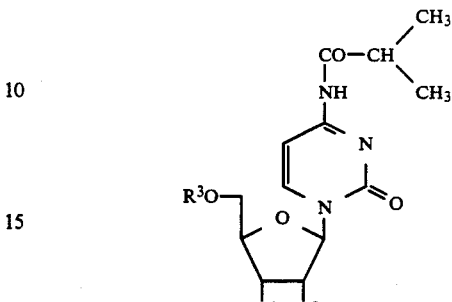

on a nucleoside or an oligonucleotide, wherein $R^3$ is selected from the group consisting of 9-phenylxanthenyl, trityl of the formula

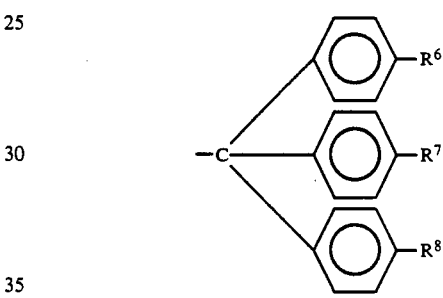

wherein $R^6$, $R^7$ and $R^8$, which may be the same or different, are hydrogen, methyl, ethyl or methoxy, $R^4$ is a phosphorylated group selected from the group consisting of phosphate, H-phosphonate and phosphoramidite; and
$R^5$ is a hydrogen atom; and 2) hydrolytically removing the group of formula:

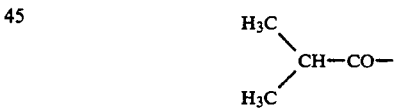

* * * * *